United States Patent [19]

Arlt et al.

[11] 4,216,162
[45] Aug. 5, 1980

[54] NOVEL DERIVATIVES OF CYCLOPROPANECARBOXYLIC ACID USEFUL AS INTERMEDIATES FOR THE PREPARATION OF INSECTICIDES

[75] Inventors: Dieter Arlt, Cologne; Manfred Jautelat, Burscheid, both of Fed. Rep. of Germany

[73] Assignee: Bayer Aktiengesellschaft, Leverkusen, Fed. Rep. of Germany

[21] Appl. No.: 920,031

[22] Filed: Jun. 28, 1978

[30] Foreign Application Priority Data

Jul. 16, 1977 [DE] Fed. Rep. of Germany ....... 2732213

[51] Int. Cl.² .................. C07C 131/11; C07C 103/19; C07C 153/063
[52] U.S. Cl. .................... 260/500.5 H; 260/453 RW; 260/455 R; 260/502.6; 260/551 S; 260/557 R; 260/557 H; 260/564 R; 260/564 G; 260/565; 548/216; 548/237; 560/124
[58] Field of Search .................... 260/557 R, 500.5 H, 260/453 RW, 551 S, 557 H, 564 R, 564 G, 565, 502.6, 455 R; 560/124

[56] References Cited

U.S. PATENT DOCUMENTS

| | | | |
|---|---|---|---|
| 3,211,544 | 10/1965 | Dubrovin | 260/557 R X |
| 3,328,156 | 6/1967 | Hopkins | 71/118 |
| 3,455,991 | 7/1969 | Bonnet | 260/557 R X |
| 3,484,485 | 12/1969 | Schwartz | 260/557 R |
| 3,753,679 | 8/1973 | Singhel | 71/98 |
| 3,919,227 | 11/1975 | Andreades et al. | 260/557 R X |
| 4,012,430 | 3/1977 | Verbrugge et al. | 260/557 R X |

FOREIGN PATENT DOCUMENTS

| | | | |
|---|---|---|---|
| 2732213 | 1/1979 | Fed. Rep. of Germany | 260/557 R |
| 49-31977 | 8/1974 | Japan | 260/557 R |

OTHER PUBLICATIONS

Farkas et al., Collect, Czechosl. Chem. Comm. 24, 2,230 (1959).

Primary Examiner—Thomas A. Waltz
Attorney, Agent, or Firm—Sprung, Felfe, Horn, Lynch & Kramer

[57] ABSTRACT

Novel 2-(2,2-dihalogenovinyl)-3,3-dimethylcyclopropanecarboxylic acid derivatives of the formula

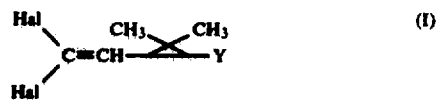

e.g. amides, thioamides, oxazolines, amidoximes and hydroxamic acids, are produced by reacting the new compounds

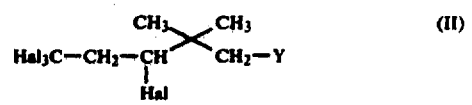

with a base in the presence of a diluent. New compounds of the formula

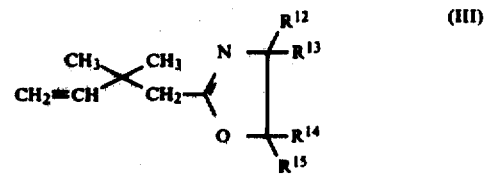

are produced by reacting

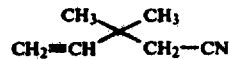

with

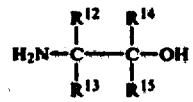

14 Claims, No Drawings

NOVEL DERIVATIVES OF CYCLOPROPANECARBOXYLIC ACID USEFUL AS INTERMEDIATES FOR THE PREPARATION OF INSECTICIDES

The present invention relates to certain new derivatives of 2-(2,2-dihalogenovinyl)-3,3-dimethylcyclopropanecarboxylic acids and to a process for their preparation.

These derivatives can be used as intermediate products for the preparation of various insecticides, such as, for example, 2-(2,2-dichlorovinyl)-3,3-dimethylcyclopropanecarboxylic acid 3-phenoxybenzyl ester.

The preparation of 2-(2,2-dichlorovinyl)-3,3-dimethylcyclopropanecarboxylic acid by reacting 1,1-dichloro-4-methyl-1,3-pentadiene with diazoacetic ester and subsequent hydrolysis is already known (Farkas et al, Collect. Czechosl. Chem. Commun. 24, 2,230 (1959)). However, this process has a number of disadvantages. Thus, the handling in industry of large quantities of diazoacetic ester, which can decompose in an explosive manner, entails considerable risks. The use of diazo compounds also creates problems from a physiological point of view.

The use of 1-cyano-2-(2,2-dichlorovinyl)-3,3-dimethylcyclopropane instead of the carboxylic acid has also been suggested as an intermediate stage for the preparation of the insecticidally active carboxylic acid esters. This nitrile can be prepared by elimination of water from the corresponding aldoxime (see German Offenlegungsschrift (German Published Specification) No. 2,621,832), or, by base-catalyzed cyclization, from 3-bromo-1-cyano-2,2-dimethyl-5,5,5-trichloropentane (see German Offenlegungsschrift (German Published Specification) No. 2,621,831). However, these processes suffer from the drawback that, even under drastic conditions, 1-cyano-2-(2,2-dichlorovinyl)-3,3-dimethylcyclopropane can only be saponified to give the corresponding carboxylic acid in low yields.

The present invention provides, as new compounds, the 2-(2,2-dihalogenovinyl)-3,3-dimethylcyclopropanecarboxylic acid derivatives of the general formula

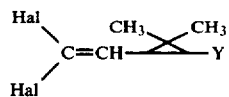  (I)

in which
Hal represents halogen, the Hal atoms being identical or different, and
Y represents a carbon atom which is linked by both a single bond to oxygen, sulphur or nitrogen and by a double bond to oxygen, sulphur or nitrogen, a least one of said bonds being taken up by nitrogen.

Preferably, Hal represents chlorine or bromine and Y represents one of the following radicals:

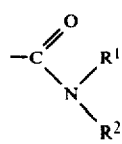  (a)

wherein
$R^1$ represents hydrogen, alkyl or aryl and
$R^2$ represents hydrogen, alkyl, aryl, hydroxyl, alkoxy, amino, alkylamino, dialkylamino, acyl, alkoxycarbonyl or aminocarbonyl, or both $R^1$ and $R^2$, conjointly with the adjacent nitrogen atom, form a heterocyclic structure, or

  (b)

wherein
$R^3$ and $R^4$ independently of one another represent hydrogen, alkyl, aryl or acyl or, conjointly with the adjacent atoms, form a heterocyclic structure, or

  (c)

wherein
$R^5$ and $R^6$ independently of one another represent hydrogen, aryl, hydroxyl, alkoxy or amino or, conjointly with the adjacent N atom, form a heterocyclic structure, or

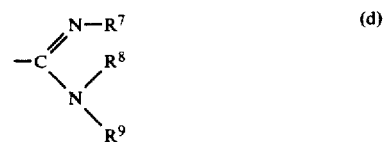  (d)

wherein
$R^7$ represents hydrogen, alkyl, aryl, amino, alkylamino, dialkylamino, hydroxyl or alkoxy and
$R^8$ and $R^9$ independently of one another represent hydrogen, alkyl, aryl, arylamino, dialkylamino or hydroxyl, or two of $R^7$, $R^8$ and $R^9$, together with the adjacent atoms, conjointly form a heterocyclic structure, or

  (e)

wherein
$R^{10}$ represents alkyl and
$R^{11}$ represents hydrogen, alkyl, aryl, hydroxyl, alkoxy or amino, or $R^{10}$ and $R^{11}$, conjointly with the adjacent atoms, form a heterocyclic structure.

Compounds which are particularly preferred are those in which Y represents a radical of the formula (a) wherein $R^1$ represents hydrogen, alkyl having 1-4 carbon atoms, phenyl or tolyl and $R^2$ represents hydrogen, alkyl having 1-4 carbon atoms, phenyl, tolyl, hydroxyl, alkoxy having 1-4 carbon atoms, amino, alkylamino having 1-4 carbon atoms, dialkylamino having 2-8 carbon atoms, acyl having 1-7 carbon atoms, alkoxycarbonyl having 2-5 carbon atoms, or aminocarbonyl, or $R^1$ and $R^2$ conjointly represent tetramethylene, pentamethylene or —$CH_2$—$CH_2$—O—$CH_2$—$CH_2$—;

or a radical of the formula (b) wherein $R^3$ represents alkyl having 1-4 carbon atoms, phenyl or acyl having 1-7 carbon atoms, $R^4$ represents hydrogen, alkyl having 1-4 carbon atoms, phenyl or acyl having 1-7 carbon atoms, or $R^3$ and $R^4$ conjointly represent an alkylene radical having 2-5 carbon atoms (such as ethylene or trimethylene);

or a radical of the formula (c) wherein $R^5$ represents hydrogen or alkyl having 1-4 carbon atoms, $R^6$ represents hydrogen, alkyl having 1-4 carbon atoms, phenyl, hydroxyl, alkoxy having 1-4 carbon atoms or amino, or $R^5$ and $R^6$ conjointly represent tetramethylene, pentamethylene or —$CH_2$—$CH_2$—O—$CH_2$—$CH_2$—;

or a radical of the formula (d) wherein $R^7$ represents hydrogen, alkyl having 1-4 carbon atoms, phenyl, alkylamino having 1-4 carbon atoms, dialkylamino having 2-8 carbon atoms, hydroxyl, or alkoxy having 1-4 carbon atoms, $R^8$ represents hydrogen or alkyl having 1-4 carbon atoms, and $R^9$ represents hydrogen, alkyl having 1-4 carbon atoms, phenyl, amino, alkylamino having 1-4 carbon atoms, dialkylamino having 2-8 carbon atoms, or hydroxyl, or $R^7$ and $R^8$ conjointly represent an alkylene radical having 2-5 carbon atoms (such as ethylene or trimethylene) or $R^8$ and $R^9$ conjointly represent tetramethylene, pentamethylene or —$CH_2$—$CH_2$—O—$CH_2$—$CH_2$—;

or a radical of the formula (e) wherein $R^{10}$ represents alkyl having 1-4 carbon atoms, and $R^{11}$ represents hydrogen, alkyl having 1-4 carbon atoms, phenyl, hydroxyl, alkoxy having 1-4 carbon atoms or amino.

The invention also provides a process for the preparation of a 2-(2,2-dihalogenovinyl)-3,3-dimethylcyclopropanecarboxylic acid derivative of the general formula (I), in which a compound of the general formula

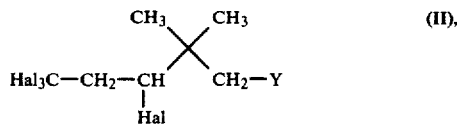

in which

Hal and Y have the meanings stated above, is treated with a base in the presence of a diluent.

The cyclopropanecarboxylic acid derivatives of the general formula (I) may be used as intermediates for the preparation of the known cyclopropanecarboxylic acids on which they are based and which, in turn, are intermediates for the preparation of known insecticides. The cyclopropanecarboxylic acids are obtained by subjecting the compounds of the general formula (I) to acid or alkaline hydrolysis under suitable conditions (Houben-Weyl, Methoden der organischen Chemie ("Methods of Organic Chemistry"), Volume VIII, page 432 (1952) and Methodicum Chimicum, Volume 5, page 572 (1975)).

The use of the cyclopropanecarboxylic acid derivatives of the general formula (I) represents a decisive improvement over the process for the preparation of cyclopropanecarboxylic acids starting from the corresponding cyclopropanecarboxylic acid nitrile. The stage of the cyclopropanecarboxylic acid nitrile, which can only be saponified with difficulty and in a low yield to give the cyclopropanecarboxylic acid or derivatives thereof, is avoided by this means.

It is surprising that the conversion of the cyano group into functional carboxylic acid derivatives can be achieved very much more easily and in a better manner by way of 4-cyano-3,3-dimethyl-1-butene, the starting material for the preparation of the compounds of the formula (I), than by way of 1-cyano-2-(2,2-dichlorovinyl)-3,3-dimethylcyclopropane. The use of the new compounds (I) according to the invention leads to a process which has the decisive advantage that the synthesis of the insecticidally active 2-(2,2-dihalogenovinyl)-3,3-dimethylcyclopropanecarboxylic acid esters, for example 2-(2,2-dichlorovinyl)-3,3-dimethylcyclopropanecarboxylic acid 3-phenoxy-benzyl ester, can be achieved more simply and with better yields than from the corresponding nitriles.

If 4,6,6,6-tetrachloro-3,3-dimethyl-n-hexanoic acid amide is used as the starting material, the course of the reaction can be represented by the following equation:

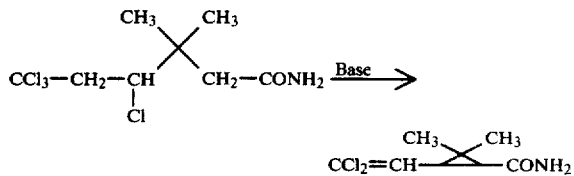

In accordance with a particular embodiment of this invention the individual reaction stages can be combined in one process in such a way that it is possible to dispense with purifying and isolating the intermediate products. Thus, for example, 3,3-dimethyl-4-pentenoic acid amide, prepared by partial hydrolysis from 4-cyano-3,3-dimethyl-1-butene, is taken up in carbon tetrachloride and, after adding dibenzoyl peroxide, is converted, by heating, into the adduct 3,3-dimethyl-4,6,6,6-tetrachlorohexanoic acid amide. After removing the solvent, the residue is taken up in ethanol and is cyclized in the presence of sodium ethylate to give 2-(2,2-dichlorovinyl)-3,3-dimethylcyclopropanecarboxylic acid amide, which is isolated and purified.

The following may be mentioned as examples of starting compounds of the general formula (II) which can be used with particular advantage for the preparation of the cyclopropanecarboxylic acid derivatives: 3,3-dimethyl-4,6,6,6-tetrachlorohexanoic acid amide, 4-bromo-3,3-dimethyl-6,6,6-trichlorohexanoic acid amide, 3,3-dimethyl-4,6,6,6-tetrabromohexanoic acid amide, 3,3-dimethyl-4,6,6,6-tetrachlorohexanoic acid N-tert.-butylamide, 3,3-dimethyl-4,6,6,6-tetrabromohexanoic acid N-tert.-butylamide, 3,3-dimethyl-4,6,6,6-tetrachlorohexanoic acid anilide, 3,3-dimethyl-4,6,6,6-tetrachlorohexanoic acid piperidide, 3,3-dimethyl-4,6,6,6-tetrachlorohexanoic acid morpholide, 3,3-dimethyl-4,6,6,6-tetrachlorohexanoic acid hydroxamic acid, 3,3-dimethyl-4,6,6,6-tetrachlorohexanoic acid hydrazide, 3,3-dimethyl-4,6,6,6-tetrachlorohexanoic acid imide ethyl ester, 3,3-dimethyl-4,6,6,6-tetrachlorohexanoic acid methylimide methyl ester, 2-(2',2'-dimethyl-3',5',5',5'-tetrachloropentyl)-oxazoline, 2-(2',2'-dimethyl-3',5',5',5'-tetrachloropentyl)-4,4-dimethyloxazoline, 2-(2',2'-dimethyl-3'-5',5',5'-tetrabromopentyl)-oxazoline, 2-(2',2'-dimethyl-3',5',5',5'-tetrachloropentyl)-5,6-dihydro-4H-1,3-oxazine, 3,3-dimethyl-4,6,6,6-tetrachlorohexanehydroximic acid O-methyl ethyl ester, 3,3-dimethyl-4,6,6,6-tetrachlorohexanethiocarboxylic acid amide, 3,3-dimethyl-4,6,6,6-tetrachlorohexanethiocarboxylic acid N-tert.-butylamide, 3,3-dimethyl-4,6,6,6-tetrachlorohexanethiocarboxylic acid N-ethylamide, 3,3-dimethyl-4,6,6,6-tetrachlorohexanoic acid amidine, 3,3-dimethyl-4,6,6,6-tetrachlorohexanoic acid N-methyl-N'-phenylamidine, 3,3-dimethyl-4,6,6,6-tetrachlorohexanoic acid amidoxime, 3,3-dimethyl-4,6,6,6-tetrachlorohexanoic acid amidrazone, 3,3-dimethyl-4,6,6,6-tetrachlorohexanethiocarboxylic acid N-methyl-hydrazonide-S-methyl ester and 3,3-dimethyl-4,6,6,6-tetrachlorohexane-S-methyl-thiohydroxamic acid.

The starting compounds of the general formula (II) are new. They can, however, be obtained by reacting compounds of the general formula

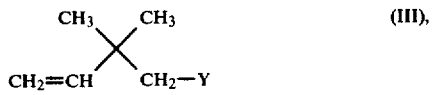

in which
Y has the meaning stated above, optionally in the presence of a diluent, with a carbon tetrahalide in the presence of a catalyst.

The course of the reaction here can be illustrated by the following equation:

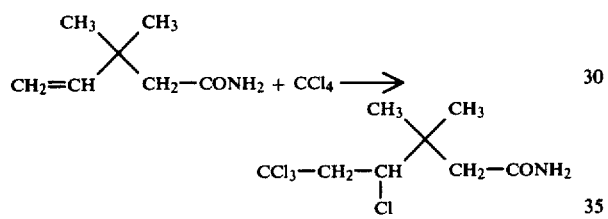

Carbon tetrahalides which are particularly preferred are carbon tetrachloride, bromotrichloromethane or carbon tetrabromide.

The addition reaction of the carbon tetrahalides with the compounds of the formula (III) is carried out within the temperature range of about 50°-120° C., preferably about 70°-100° C., using catalysts such as dibenzoyl peroxide, azobisisobutyronitrile, copper salts or iron salts.

Suitable diluents are all inert organic solvents, such as hydrocarbons, ethers, nitriles, esters or ketones. It is preferable, however, to use an excess of the carbon tetrahalides which are to be used as the starting materials.

Some of the starting compounds of the general formula (III) are new. They can be obtained (a) by converting the nitrile group of 4-cyano-3,3-dimethyl-1-butene, in a manner which is in itself known, into the radical Y of the compounds of the general formula (III) (see Houben Weyl, Methoden der Organischen Chemie ("Methods of Organic Chemistry"), Volume VIII and Methodicum Chimicum, Volume 6, 1974, Thieme Verlag Stuttgart) or (b) by converting the carboxyl radical of 3,3-dimethyl-4-pentenoic acid, in a manner which is in itself known, into the radical Y of the compounds of the general formula (III) (see Houben Weyl, Methoden der Organischen Chemie ("Methods of Organic Chemistry"), Volume VIII and Methodicum Chimicum, Volume 6, 1974, Thieme Verlag Stuttgart).

The process for the preparation of the 2-(2,2-dihalogenovinyl)-3,3-dimethylcyclopropanecarboxylic acid derivatives according to the invention is generally carried out by the action of at least two moles of a base per mole of the compound of the formula (II) and gives the compounds according to the invention by cyclization and β-elimination. In this process, cyclization and β-elimination can be carried out either successively or simultaneously.

Suitable bases are tertiary amines, for example pyridine, triethylamine, dimethylaniline, benzyldimethylamine, N-methylpiperidine or 1,8-diazabicyclo(5,4,0)-undecene; alkali metal alcoholates, for example sodium methylate, sodium ethylate and potassium t-butylate; alkali metal hydroxides, such as sodium hydroxide or potassium hydroxide; alkali metal carbonates; and alkaline earth metal carbonates.

Suitable diluents are alcohols, such as methanol, ethanol or t-butanol; ethers, such as dioxane or diethyl ether; and polar solvents, such as acetonitrile, dimethylformamide, dimethylsulphoxide or hexamethylphosphoric acid triamide.

The reaction temperature can be varied within a fairly wide range. In general, the reaction is carried out between about 20° and 120° C., preferably between about 40° and 80° C.

Compounds of the general formula III

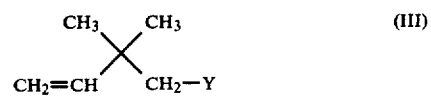

in which
Y represents a radical of the formula IV

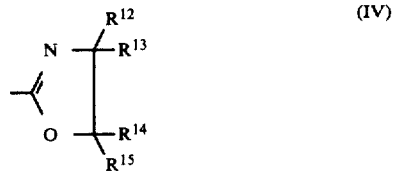

wherein
$R^{12}$–$R^{15}$ independently of one another represent hydrogen, alkyl, aralkyl, aryl or together with the adjacent atoms conjointly form a carbocyclic ring, are new.

They can be obtained by reacting 4-cyano-3,3-dimethyl-1-butene of the formula V

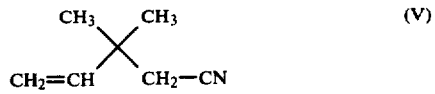

and 2-aminoalkanols of the formula VI

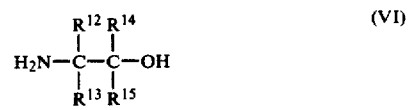

wherein
$R^{12}$–$R^{15}$ have the above mentioned meaning optionally at temperatures between about 150° and 200° C. and optionally in the presence of a catalyst and/or diluent.

Preferred compounds of the general formula III are those in which the radicals $R^{12}$–$R^{15}$ of the oxazoline-radical of formula IV represent independently of one another hydrogen, $C_{1-4}$-alkyl, $C_{7-9}$-aralkyl, phenyl being optionally substituted by halogen, $C_{1-4}$-alkoxy or phenoxy, or $R^{12}$ and $R^{13}$ or $R^{14}$ and $R^{15}$ form an alkylene-chain with 4 to 6 carbon atoms or $R^{13}$ and $R^{15}$ form an alkylene-chain with 3 to 4 carbon atoms.

Preferred examples are 2-(2,2-dimethyl-3-buten-1-yl)-2-oxazoline
2-(2,2-dimethyl-3-buten-1-yl)-4,4-dimethyl-2-oxazoline
2-(2,2-dimethyl-3-buten-1-yl)-5,5-dimethyl-2-oxazoline
2-(2,2-dimethyl-3-buten-1-yl)-4,4,5,5-tetramethyl-2-oxazoline,
2-(2,2-dimethyl-3-buten-1-yl)-5-benzyl-2-oxazoline
2-(2,2-dimethyl-3-buten-1-yl)-4,4-tetramethylene-2-oxazoline
2-(2,2-dimethyl-3-buten-1-yl)-4,5-tetramethylene-2-oxazoline
2-(2,2-dimethyl-3-buten-1-yl)-4-phenyl-2-oxazoline
2-(2,2-dimethyl-3-buten-1-yl)-5-phenyl-2-oxazoline
2-(2,2-dimethyl-3-buten-1-yl)-5-(m-phenoxyphenyl)-2-oxazoline.

The novel compounds according to general formula III are prepared in a manner which is in itself known (see Angew. Chem., Vol. 88, page 321 (1976)). Preferred catalysts in this reaction are cadmium acetate, zinc acetate, manganese acetate, zinc chloride, copper (II) chloride, cobalt acetate or lithium chloride.

The present invention is illustrated by means of the examples which follow. In these, the formation of the radical Y, that is to say the carboxylic acid derivative group, starting from 4-cyano-3,3-dimethyl-1-butene or 3,3-dimethyl-4-pentenoic acid, is described in part 1 of each example.

The addition reaction of the carbon tetrahalide to the double bond of the starting material, which is obtained by the process described in part 1, is described in part 2 of each example.

Finally, the cyclization and β-elimination from the products obtained in accordance with part 2 is described in part 3 of each example.

EXAMPLE 1

Preparation of 2-(2,2-dichlorovinyl)-3,3-dimethylcyclopropanecarboxylic acid amide 1.1  10.9 g (0.1 mol) of 4-cyano-3,3-dimethyl-1-butene were stirred for 15 hours at 40° C. with 100 ml of 10% strength hydrogen peroxide solution, 100 ml of acetone and 15 ml of 10% strength sodium carbonate solution. The solution was then diluted with water and extracted by shaking several times with carbon tetrachloride.

1.2  After adding 0.5 g of dibenzoyl peroxide, the solution of the amide in carbon tetrachloride was heated under reflux for 12 hours. Excess carbon tetrachloride was stripped off in vacuo and the residue was taken up in 100 ml of ethanol.

1.3  0.2 mol of sodium ethylate, in the form of a solution, was added to this solution and the mixture was heated under reflux for 2 hours. The solution was diluted with methylene chloride and extracted by shaking several times with water. After drying and stripping off the solvent, 2-(2,2-dichlorovinyl)-3,3-dimethylcyclopropanecarboxylic acid amide was obtained with a melting point of 78°–81° C.

EXAMPLE 2

Preparation of 2-(2'-(2,2-dichlorovinyl)-3',3'-dimethylcyclopropyl)-oxazoline 2.1  10.9 g (0.1 mol) of 4-cyano-3,3-dimethyl-1-butene were heated to 150°–160° C. with 6.7 g (0.11 mol) of aminoethanol, with cadmium acetate as catalyst, until the evolution of $NH_3$ was complete. After cooling, the reaction mixture was taken up in carbon tetrachloride.

2.2  0.5 g of dibenzoyl peroxide was added to this solution of 2-(2',2'-dimethyl-3'-butenyl)-oxazoline in $CCl_4$ and the mixture was heated under reflux for 15 hours. The solvent was stripped off in vacuo and the residue was dissolved in 100 ml of DMSO.

2.3  After adding 24 g (0.21 mol) of potassium t-butylate, the mixture was heated at 70° C. for 1 hour. The solution was diluted with methylene chloride and extracted by shaking several times with water. After drying and stripping off the solvent in vacuo, 2-(2'-(2,2-dichlorovinyl)-3',3'-dimethylcyclopropyl)-oxazoline was obtained with a boiling point of 86°–88° C./1 mm.

EXAMPLE 3

Preparation of 2-(2,2-dichlorovinyl)-3,3-dimethylcyclopropanecarboxylic acid N-tert.-butylamide 3.1  10.9 g (0.1 mol) of 4-cyano-3,3-dimethyl-1-butene and 7.2 g (0.1 mol) of tert.-butanol were added dropwise at 15° C. to a mixture of 100 ml of glacial acetic acid and 10 g (0.1 mol) of concentrated sulphuric acid and the mixture was stirred overnight at room temperature. The solution was poured onto ice, rendered alkaline and extracted with $CH_2Cl_2$. After evaporating off the solvent, 3,3-dimethyl-4-pentenecarboxylic acid N-tert.-butylamide of melting point 73°–75° C. remained; this was dissolved in 40 g of bromotrichloromethane.

3.2  This solution was heated at 90° C. for 15 hours, adding a total of 0.5 g of dibenzoyl peroxide periodically. Excess bromotrichloromethane was distilled off in vacuo and the residue was dissolved in 100 ml of hexamethylphosphoric acid triamide.

3.3  33 g (0.3 mol) of potassium t-butylate were added to the above solution and the mixture was heated at 80° C. for 6 hours. The solution was diluted with water and extracted several times with methylene chloride. After drying and stripping off the solvent in vacuo, 2-(2,2-dichlorovinyl)-3,3-dimethylcyclopropanecarboxylic acid N-tert.-butylamide was obtained with a melting point of 108°–109° C.

EXAMPLE 4

Preparation of 2-(2,2-dimethylvinyl)-3,3-dimethylcyclopropanethiocarboxylic acid N-t-butylamide 4.1  9.15 g (50 mmol) of 3,3-dimethyl-4-pentenoic acid N-tert.-butylamide of melting point 73°–75° C. (see Example 3.1) were heated under reflux for 1 hour with 5 g of phosphorus pentasulphide in 100 ml of pyridine. The solution was filtered and the pyridine was distilled off in vacuo. The residue was taken up in carbon tetrachloride.

4.2  This solution was heated under reflux for 12 hours, 0.5 g of dibenzoyl peroxide being added incrementally. The carbon tetrachloride was stripped off in vacuo and the residue was dissolved in 100 ml of tert.-butanol.

4.3  17 g (0.15 mol) of potassium t-butylate were added and the solution was heated under reflux for 2 hours. After cooling, the reaction mixture was diluted with methylene chloride and thoroughly extracted by shaking with water. The organic phase was dried and distilled in vacuo. The residue was 2-(2,2-dichlorovinyl)-3,3-dimethylcyclopropanethiocarboxylic acid N-t-butylamide.

EXAMPLE 5

Preparation of 2-(2,2-dichlorovinyl)-3,3-dimethylcyclopropanecarboxylic acid amidoxime 5.1  4 g (0.12 mol) of hydroxylamine in 100 ml of n-butanol were stirred with 10.9 g (0.1 mol) of 4-cyano-3,3-dimethyl-1-butene for 48 hours at 40° C. The n-butanol was then distilled off in vacuo and the residue was dissolved in carbon tetrachloride.

5.2  This solution was heated under reflux for 12 hours, a total of 0.5 g of dibenzoyl peroxide being added periodically. The solvent was then stripped off and the residue was taken up in ethanol.

5.3  After adding 0.3 mol of sodium ethylate, the ethanolic solution was heated under reflux for 3 hours. The solution was then concentrated in vacuo, diluted with ether and thoroughly extracted by shaking with water. After drying and evaporating off the ether, 2-(2,2-dichlorovinyl)-3,3-dimethylcyclopropanecarboxylic acid amidoxime was obtained.

EXAMPLE 6

Preparation of 2-(2,2-dichlorovinyl)-3,3-dimethylcyclopropane hydroxamic acid 6.1  12.8 g (0.1 mol) of 3,3-dimethyl-4-pentenoic acid (J. Org.Chem. 27, 3,602 (1962)) were esterified azeotropically for 8 hours by boiling with 50 ml of ethanol and with the addition of a trace of p-toluenesulphonic acid. A solution of 3.3 g of hydroxylamine in 20 ml of ethanol and also 0.01 mol of sodium ethylate were then added and the mixture was stirred at room temperature for 24 hours. The solution was neutralized with dilute hydrochloric acid and concentrated in vacuo. The residue was extracted with carbon tetrachloride.

6.2  This solution was heated under reflux for 15 hours, 0.5 g of benzoyl peroxide being added incrementally. The solvent was then stripped off and the residue was dissolved in ethanol.

6.3  0.3 mol of sodium ethylate was added to this solution and the mixture was heated under reflux for 4 hours. It was then concentrated in vacuo, acidified with dilute hydrochloric acid and extracted with ether. The ether solution was washed with water and was then dried and concentrated on a rotary evaporator. The residue was 2-(2,2-dichlorovinyl)-3,3-dimethylcyclopropanehydroxamic acid.

It will be appreciated that the instant specification and examples are set forth by way of illustration and not limitation, and that various modifications and changes may be made without departing from the spirit and scope of the present invention.

What we claim is:

1. A 2-(2,2-dihalogenovinyl)-3,3-dimethylcyclopropanecarboxylic acid derivative of the formula

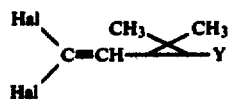

in which
Hal each independently is halogen, and
Y is

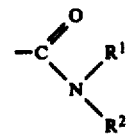
(a)

wherein $R^1$ represents hydrogen, alkyl, or aryl and $R^2$ represents hydrogen, alkyl, aryl, hydroxyl, alkoxy, amino, alkylamino, dialkylamino, acyl, alkoxycarbonyl, or aminocarbonyl, or Y is

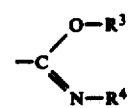
(b)

wherein $R^3$ and $R^4$ independently of one another represent hydrogen, alkyl, aryl, or acyl, or Y is

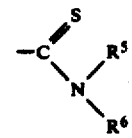
(c)

wherein $R^5$ and $R^6$ independently of one another represent hydrogen, aryl, hydroxyl, alkoxy, or amino, or Y is

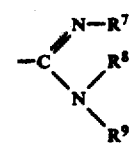
(d)

wherein $R^7$ represents hydrogen, alkyl, aryl, amino, alkylamino, dialkylamino, hydroxyl, or alkoxy and $R^8$ and $R^9$ independently of one another represent hydrogen, alkyl, aryl, arylamino, dialkylamino, or hydroxyl, or Y is

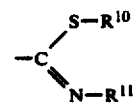
(e)

wherein $R^{10}$ represents alkyl and $R^{11}$ represents hydrogen, alkyl, aryl, hydroxyl, alkoxy, or amino.

2. A compound according to claim 1, in which Y represents a radical of the formula (a) wherein $R^1$ represents hydrogen, alkyl having 1–4 carbon atoms, phenyl or tolyl and $R^2$ represents hydrogen, alkyl having 1–4 carbon atoms, phenyl, tolyl, hydroxyl, alkoxy having 1–4 carbon atoms, amino, alkylamino having 1–4 carbon atoms, dialkylamino having 2–8 carbon atoms, acyl having 1–7 carbon atoms, alkoxycarbonyl having 2–5 carbon atoms, or aminocarbonyl;

or a radical of the formula (b) wherein $R^3$ represents alkyl having 1–4 carbon atoms, phenyl or acyl having 1–7 carbon atoms, $R^4$ represents hydrogen, alkyl having 1–4 carbon atoms, phenyl or acyl having 1–7 carbon atoms;

or a radical of the formula (c) wherein $R^5$ represents hydrogen or alkyl having 1–4 carbon atoms, $R^6$ represents hydrogen, alkyl having 1–4 carbon atoms, phenyl, hydroxyl, alkoxy having 1–4 carbon atoms or amino;

or a radical of the formula (d) wherein $R^7$ represents hydrogen, alkyl having 1–4 carbon atoms, phenyl, alkylamino having 1–4 carbon atoms, dialkylamino having 2–8 carbon atoms, hydroxyl, or alkoxy having 1–4 carbon atoms, $R^8$ represents hydrogen or alkyl having 1–4 carbon atoms, and $R^9$ represents hydrogen, alkyl having 1–4 carbon atoms, phenyl, amino, alkylamino having 1–4 carbon atoms, dialkylamino having 2–8 carbon atoms, or hydroxyl;

or a radical of the formula (e) wherein $R^{10}$ represents alkyl having 1–4 carbon atoms, and $R^{11}$ represents hydrogen, alkyl having 1–4 carbon atoms, phenyl, hydroxyl, alkoxy having 1–4 carbon atoms or amino.

3. A compound according to claim 1, wherein such compound is 2-(2,2-dichlorovinyl)-3,3-dimethylcyclopropanecarboxylic acid amide.

4. A compound according to claim 1, wherein such compound is 2-(2,2-dichlorovinyl)-3,3-dimethylcyclopropanecarboxylic acid N-tert.-butylamide.

5. A compound according to claim 1, wherein such compound is 2-(2,2-dimethylvinyl)-3,3-dimethylcyclopropanethiocarboxylic acid N-t-butylamide.

6. A compound according to claim 1, wherein such compound is 2-(2,2-dichlorovinyl)-3,3-dimethylcyclopropanecarboxylic acid amidoxime.

7. A compound according to claim 1, wherein such compound is 2-(2,2-dichlorovinyl)-3,3-dimethylcyclopropane hydroxamic acid.

8. A process for the preparation of a 2-(2,2-dihalogenovinyl)-3,3-dimethylcyclopropanecarboxylic acid derivative according to claim 1, comprising reacting a compound of the formula

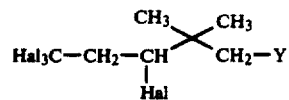

with a base in the presence of a diluent.

9. A process according to claim 8, in which at least about two moles of a base selected from the group consisting of a tertiary amine, an alkali metal alcoholate, an alkali metal hydroxide, an alkali metal carbonate and an alkaline earth metal carbonate are employed per mole of the compound of the formula

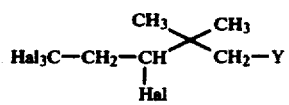

10. A process according to claim 8, in which the base is pyridine, triethylamine, dimethylaniline, benzyldimethylamine, N-methylpiperidine, 1,8-diazabicyclo(5,4,0)undecane, sodium methylate, sodium ethylate, potassium t-butylate, sodium hydroxide or potassium hydroxide.

11. A process according to claim 8, in which the diluent is an alcohol, an ether or a polar organic solvent.

12. A process according to claim 8, in which the diluent is methanol, ethanol, t-butanol, dioxane, diethyl ether, acetonitrile, dimethylformamide, dimethylsulphoxide or hexamethylphosphoric acid triamide.

13. A process according to claim 8, in which the reaction is effected at from about room temperature to 120° C.

14. A process according to claim 10, in which at least about two moles of the base are employed per mole of the compound of the formula

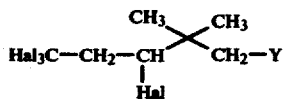

* * * * *